(12) United States Patent
Tan et al.

(10) Patent No.: US 8,759,546 B2
(45) Date of Patent: Jun. 24, 2014

(54) PHYSICAL NANO-COMPLEXES FOR PREVENTING AND TREATING CANCER AND METHOD FOR MANUFACTURING THE SAME

(75) Inventors: Shan-Wen Tan, Taipei (TW);
Ming-Kung Yeh, Taipei (TW); Dar-Shih Hsieh, Taichung (TW); Chang-Jer Wu, Taipei (TW)

(73) Assignee: Gold Nanotech Inc. (TW)

( * ) Notice: Subject to any disclaimer, the term of this patent is extended or adjusted under 35 U.S.C. 154(b) by 0 days.

(21) Appl. No.: 13/468,163

(22) Filed: May 10, 2012

(65) Prior Publication Data
US 2013/0190515 A1    Jul. 25, 2013

(30) Foreign Application Priority Data

Jan. 20, 2012 (TW) .............................. 101102498 A (51) Int. Cl.
*C07D 311/62*    (2006.01)

(52) U.S. Cl.
USPC ........................................................ 549/400

(58) Field of Classification Search
USPC ........................................................ 549/400
See application file for complete search history.

(56) References Cited

U.S. PATENT DOCUMENTS

2009/0074674 A1*    3/2009    Katti et al. ................... 424/9.42

OTHER PUBLICATIONS

By Imtiaz A. Siddiqui, Vaqar M. Adhami, Dhruba J. Bharali, et al. Cancer Res 2009;69:1712-1716. Published OnlineFirst Feb. 17, 2009.*
Priyabrata Mukherjee, Resham Bhattacharya, Ping Wang, et al. Clin Cancer Res 2005;11:3530-3534. Published online May 2, 2005.*
Rieger-Christ et al. Journal of Cellular biochemistry 102 (2007) 377-388.*
Leppart et al. European Urology 49 (2006) 226-234.*
Hsieh et al.International Journal of Nanomedicine 7 (2012) 1623-1633.*
Hsieh et al. Biomaterials 32 (2011) 7633-7640.*
Zhu et al. Phytochemistry, vol. 44, No. 3 (1997) pp. 441-447.*
MedicineNet.com (http://www.medterms.com, 2004).*

* cited by examiner

*Primary Examiner* — Golam M M Shameem
*Assistant Examiner* — Laura Daniel (57) ABSTRACT

The present invention discloses a physical nano-complex for preventing and treating cancer and a method for manufacturing the same. The composition contains EGCG and nanogold, wherein the ratio of the EGCG to the nanogold is in a range from 23:0.5~23:10 (ppm/ppm). The present invention further discloses a method for manufacturing the composition, wherein the method is to mix the EGCG and the nanogold sufficiently by an ultrasonication process, which makes the EGCG and the nanogold combine to each other well.

9 Claims, 10 Drawing Sheets

|  | IC50, mean ± SD | |
| --- | --- | --- |
|  | Vero | MBT-2 |
| EGCG (µM) | 127.28 ± 4.38 | 28.48 ± 6.21 |
| pNG (ppm) | 13.67 ± 2.68 | 4.35 ± 5.88 |

| Reagents | Percent cells in phase | | |
|---|---|---|---|
| | $G_0/G_1$ | S | $G_2/M$ |
| Control | 76.0±0.4 | 14.4±0.4 | 9.6±0.4 |
| E12.5 | 67.9±0.5 | 26.5±0.6 | 5.6±0.4 |
| E25 | 66.6±0.5 | 28.6±0.3 | 4.8±0.5 |
| E50 | 79.1±0.4 | 15.8±0.5 | 5.1±0.4 |
| pNG0.5 | 73.5±0.3 | 21.4±0.3 | 5.1±0.3 |
| pNG1 | 68.1±0.3 | 25.9±0.4 | 6.0±0.5 |
| pNG2 | 67.2±0.3 | 27.6±0.4 | 5.2±0.4 |
| E50pNG2 | 86.7±0.5 | 7.8±0.4 | 5.5±0.4 |

PHYSICAL NANO-COMPLEXES FOR PREVENTING AND TREATING CANCER AND METHOD FOR MANUFACTURING THE SAME

BACKGROUND OF THE INVENTION

1. Field of the Invention

The present invention relates to physical nano-complexes for preventing and treating cancer and a method for manufacturing the same, and more particularly to physical complexes containing a specific ratio of EGCG and nanogold, and a manufacturing method for sufficiently mixing EGCG and nanogold by a physical process, so that the complexes can be used to prevent and treat various kinds of cancer.

2. Description of the Prior Art

Many naturally occurring phenolic compounds/substances as well as biotechnological products are receiving increasing attention on anti-oxidation and have proven to be effective antioxidants in biological systems. Many of the cancer chemopreventive properties of green tea are mediated by epigallocatechin-3-gallate (EGCG), a phenolic compound that induces apoptosis and arrests cell growth. Green tea enhances humoral and cell-mediated immunity, decreases the risk of certain cancers, and has certain advantages in treating inflammatory disorders. EGCG and its derivatives are some of the most important candidates for the development of effective and nontoxic medicines with strong free-radical scavenging and antioxidant actions. Many studies indicate that EGCG involved in prevention and treatment of many cancers, such as bladder, breast, prostate and colon cancers. Albeit EGCG has many desirable anti-tumorigenic properties as exemplified in human and animal models, some adverse effects, such as hepatitis, resulting in excessive consumption of EGCG have been reported. Given these facts, using EGCG as an anti-tumorigenic agent in clinics should ponder how to deliver EGCG to the right target site and to maintain an appropriate cell fluid level.

In recent years, the development of nanomedicine has soared. Nanomedicine involves the utilization of nanotechnology for the benefit of human health and well being. The use of nanotechnology in various sectors of therapeutics has revolutionized the field of medicine. Metal nanoparticles are new-generation materials being widely investigated for biomedical and therapeutic applications, including their use in diagnostics, therapeutics, and biomedical tools for research. In the case of physical nanogold particles (pNGs), size, shape, surface chemistry, and optical properties are parameters under control. They also have very unique and exciting capabilities, such as comparable size with biomolecules and the ability to bind to various molecules, making them potential candidates used in chemical and biological applications, such as NG-based drug delivery, cell-specific targeting, and controlled drug release. By taking advantage of their optical-electronic properties, numerous proven applications for NGs have shown promising results in the use in medicinal applications, including plasmon-based labeling and imaging, optical and electrochemical sensing, diagnostics, and therapy for various diseases and cancer.

In view of this, it is necessary to provide a new composition for effectively preventing and treating cancer, wherein the physical nano-complexes having the property of anti-cancer of EGCG, and the EGCG can be accurately delivered to cancer cells by the property of drug delivery and cell specificity of nanogold, so as to increase the treating effect to cancer.

SUMMARY OF THE INVENTION

In view of the above shortcomings of the prior art, the inventor of the present invention resorted to past experience, imagination, and creativity, performed experiments and researches repeatedly, and eventually devised the present invention, a physical nano-complex for preventing and treating cancer and a method for manufacturing the same.

Therefore, it is a primary objective of the present invention to provide physical nano-complexes for preventing and treating cancer, which can enhance the treating effect of cancer by the composition simultaneously containing the properties of EGCG and nanogold.

According to the above objective, the present invention provides a physical nano-complex for preventing and treating cancer comprising EGCG and nanogold, wherein the ratio of EGCG to nanogold is in a range of 23:0.5~23:10 (ppm/ppm).

Another objective of the present invention is to provide a method for manufacturing the composition for preventing and treating cancer, which mixes the EGCG and the nanogold sufficiently by a physical process for combining the EGCG with nanogold tightly, and controlling the related concentration effectively, so that the effects of preventing and treating cancer can be maximized.

According to the above objective, the present invention provides a method for manufacturing a composition for preventing and treating cancer comprising the steps of: (1) providing EGCG and nano-metal; (2) mixing the EGCG and the nano-metal; (3) centrifuging the product of step (2) by 14000 rpm for 2 hours, and then removing supernatant; (4) dissolving pellet in step (3) by deionized water; (5) repeating steps (3) and (4) for two times; and (6) analyzing the concentration of the EGCG and the nano-metal.

BRIEF DESCRIPTION OF THE DRAWINGS

For a complete understanding of the aspects, structures and techniques of the invention, reference should be made to the following detailed description and accompanying drawings wherein.

DETAILED DESCRIPTION OF THE PREFERRED EMBODIMENTS

Firstly, the composition for preventing and treating cancer is introduced. The physical nano-complexes of the present invention for preventing and treating cancer comprises a specific amount of EGCG and nano-metal, wherein the nano-metal is physical, chemical or biological nanogold, and the particle size is 1.0 nm-50 nm. The ratio of EGCG to nanogold is in a range of 23:0.5~23:10 (ppm/ppm), wherein the optimal ratio of EGCG to nanogold is 23:2.5 (ppm/ppm). The physical nano-complexes of the present invention has the treatment effect to various cancer, such as bladder cancer, skin cancer, stomach cancer, colon cancer, breast cancer, prostate cancer, oral cancer, and lung cancer. The composition contains many properties, including acid resistance, inhibiting the vascular proliferation, promoting the immune system to resist cancer, and promoting the nature killer cells to resist cancer, wherein the mechanism of the composition inhibiting cancer cells is through cytotoxicity, growth inhibition, vascular proliferation inhibition, immune system promotion, and nature killer cells promotion. Generally, catechin includes EGCG (epigallocatechin gallate), EGC (epigallocatechin), C (catechin), EC (epicatechin), and ECG (epicatechin gallate).

Figure 1:
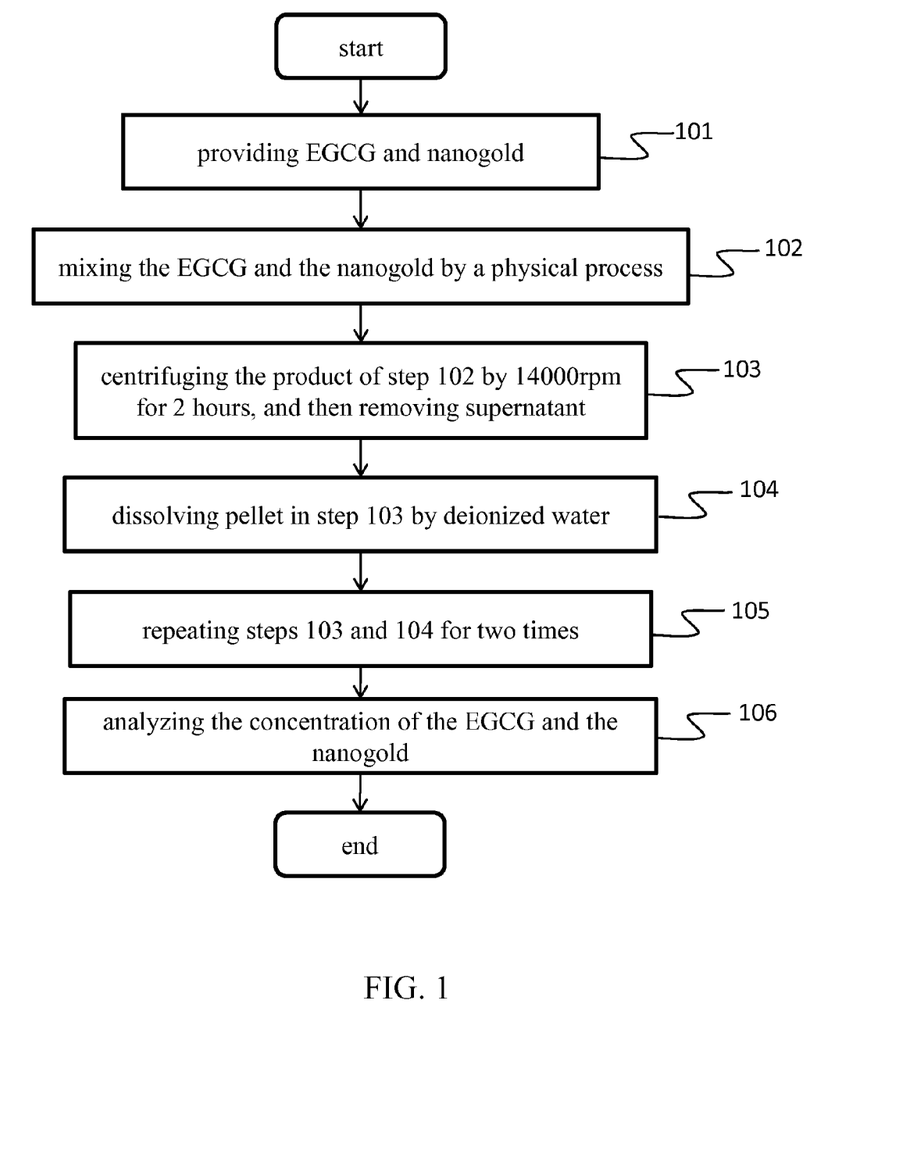
FIG. 1 is a flow chart for manufacturing a physical nano-complex for preventing and treating cancer.

Referring to FIG. 1, which is a flow chart for manufacturing a composition for preventing and treating cancer. The method for manufacturing the composition for preventing and treating cancer comprises the steps of: (step 101) providing EGCG and nanogold, wherein the ratio of EGCG to nanogold is in a range of 23:0.5~23:10 (ppm/ppm), and wherein the optimal ratio of EGCG to nanogold is 23:2.5 (ppm/ppm); (step 102) mixing the EGCG and the nanogold by a physical process, wherein the physical process is an ultrasonication process, and the ultrasonication process is to vibrate the mixture by ultrasonic under room temperature for 5 min; (step 103) centrifuging the product of step 102 by 14000 rpm for 2 hours, and then removing supernatant; (step 104) dissolving pellet in step 103 by deionized water; (step 105) repeating steps 103 and 104 for two times; and (step 106) analyzing the concentration of the EGCG and the nanogold, so as to confirm the concentration and the ratio of EGCG and nanogold.

Bladder cancer is one of the most common cancers. There were approximate 70,980 cases diagnosed with bladder cancer in the United States in 2009, of which 14,330 patients would likely succumb to the disease. Intravesical chemotherapy by infusing drugs through urethra into bladder is the most common way to treat the early-state bladder cancer. With the disease progressing, chemotherapy remains to be the main treatment before (neoadjuvant therapy) or after (adjuvant therapy) cancer surgery. However, side effects, including abdominal pain, anemia, bladder irritation, blurred vision, excessive bleeding or bruising, fatigue, headache, infection, loss of appetite, nausea and vomiting, would arise, which can be severe.

In order to confirm whether the composition having effect of preventing and treating cancer, the inventor use bladder cancer as the subject matter of the research, and treat the bladder cancer cells by the composition of the present invention, and then perform several related experiments and tests.

1. Antioxidant Activity of EGCG-Manogold

Figure 2:
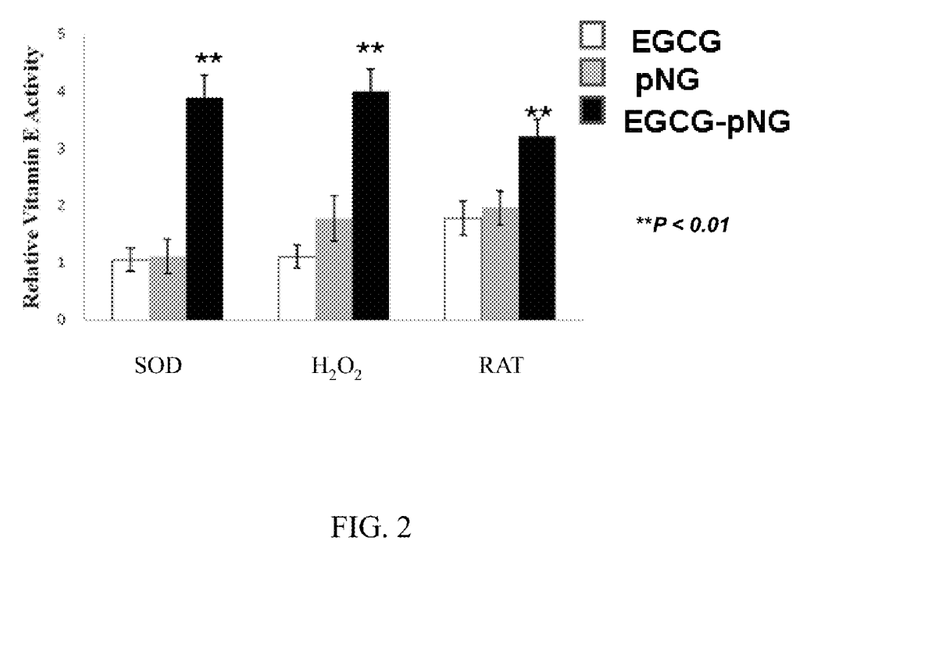
FIG. 2 is a schematic diagram of the anti-oxidant effect of the EGCG-nanogold complexes.

Refer to FIG. 2 for a schematic diagram of the anti-oxidant effect of the EGCG-nanogold complexes. This experiment shows the superoxide radical scavenging effect, hydroxyl radical effect, and the effects of EGCG-nanogold (23:2.5 ppm) on $H_2O_2$-induced hemolysis of rat erythrocytes and lipid peroxidation in rat liver microsomes.

The result indicates that The EGCG, nanogold, and EGCG-nanogold conjugates showed significant superoxide radical scavenging activity compared to vitamin E alone.

In the process of $H_2O_2$-induced erythrocyte hemolysis, $H_2O_2$ reacts with $Fe^{2+}$ in erythrocytes to form hydroxyl free radicals, which induces substantial hemolysis. As such, the results of this erythrocyte hemolysis experiment were consistent with that of the hydroxyl free radical scavenging experiment.

Lipid peroxidation is a complex process. It involves the formation and propagation of lipid peroxide and the eventual destruction of membrane lipids, producing breakdown products such as malondialdehyde in microsomes. In the present study, we adopted the $Fe^{2+}$/vitamin E system to induce the production of microsomal peroxyl radicals. EGCG-pNGs demonstrated the strongest ability (about 4-fold greater than native cells) to scavenge lipid peroxyl radicals.

2. In Vitro Anti-Tumor Activity of EGCG and Nanogold

Figure 3:
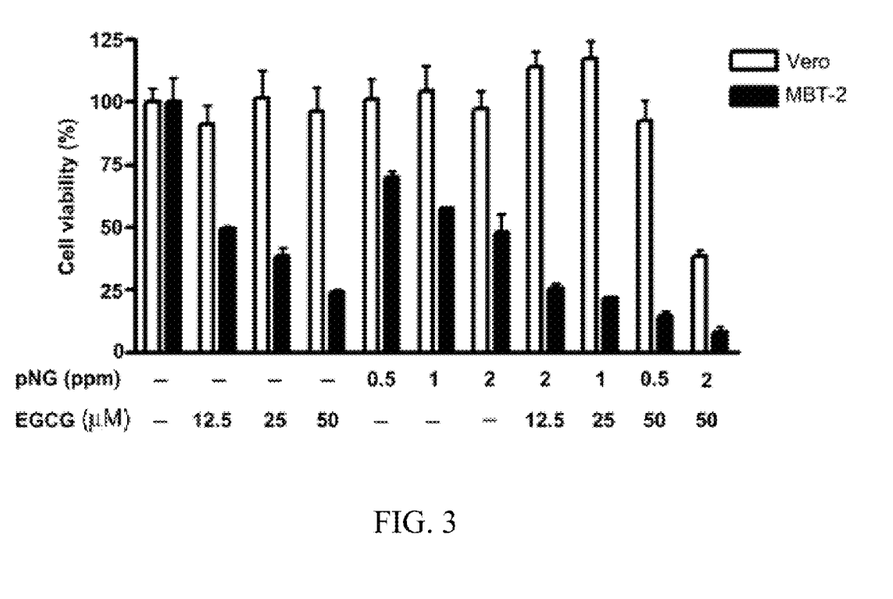
FIG. 3 is a schematic diagram of the cell viability of Vero cells and MBT-2 cells under different treating concentration of EGCG and nanogold.
Figure 4:
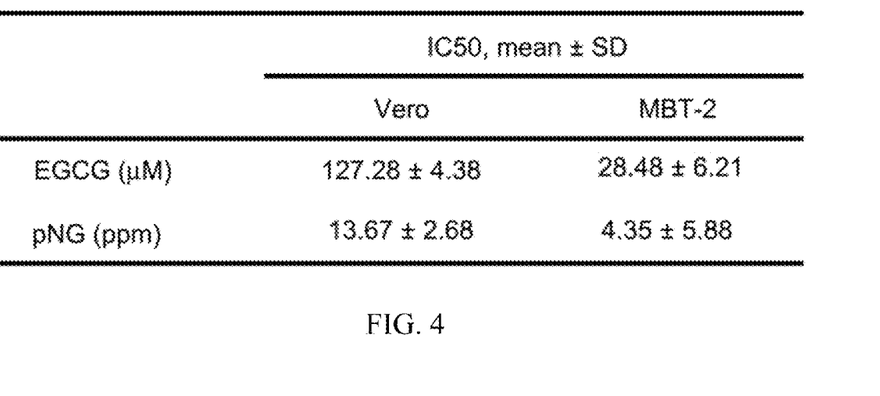
FIG. 4 is a schematic diagram of the concentrations of EGCG and nanogold mediated the 50% of cell growth inhibition of Vero cell and MBT-2 cell (IC50)

Firstly, to evaluate the tumor cytotoxicity of EGCG and/or nanogold, we examined viabilities of bladder cancer cells (MBT-2) and African green monkey kidney cells (Vero cell acts as a normal cell) at 48 hour post-EGCG or -nanogold treatment. Referring to FIG. 3, which is a schematic diagram of the cell viability of Vero cells and MBT-2 cells under different treating concentration of EGCG and nanogold. EGCG and/or nanogold were found to reduce the viability of MBT-2 cells in a concentration-dependent manner. Refer to FIG. 4 for a schematic diagram of the concentrations of EGCG and nanogold mediated the 50% of cell growth inhibition of Vero cell and MBT-2 cell (IC50). The inhibitory concentrations at 50% effect level (IC50) for EGCG and nanogold against bladder cancer cell (MBT-2) lines were determined to be 28.4 M and 4.3 ppm, respectively. In contrast, the Vero cell numbers were not changed in the presence of EGCG or nanogold. To determine whether EGCG in conjunction with nanogold has a synergistic effect on antitumorigenesis, we examined viable cell numbers after various combinations of EGCG and nanogold were added into MBT-2 cell lines. The result turned out that EGCG and nanogold are in a combination of 12.5 M and 2 ppm, respectively, significantly reducing MBT-2 cell numbers to 25.5% of the control, whereas the cell numbers in the presence of EGCG or nanogold alone were reduced to 49.7% and 48.1% of the control, respectively. As a result, the EGCG and nanogold added together do give a synergistic effect on the MBT-2 cell suppression.

3. In Vivo Anti-Tumor Activity of EGCG and Nanogold

Figure 5:
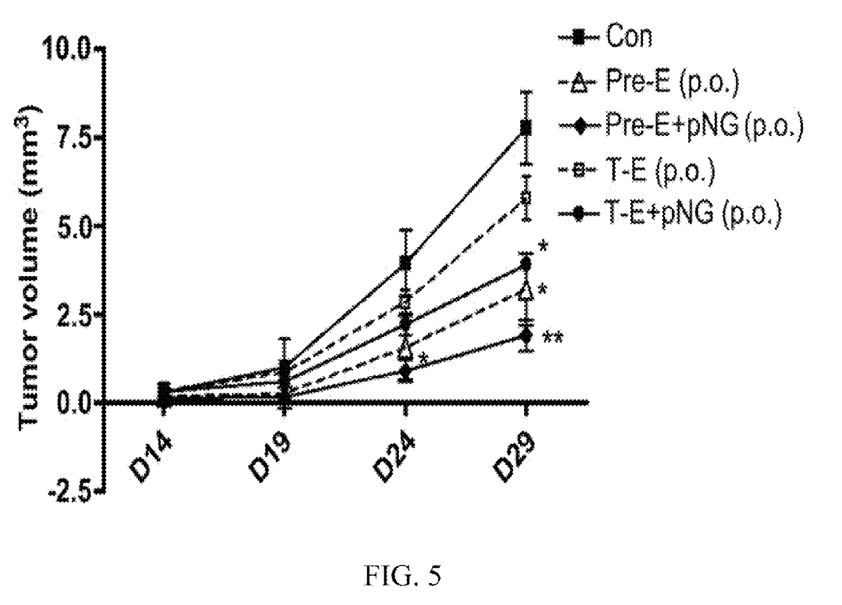
FIG. 5 is a schematic diagram of the tumor volume in mice orally treated with EGCG and/or nanogold.

Since EGCG-nanogold has been shown to be effective in suppressing the growth of tumor cells in vitro, we went on to examine its efficacy and safety in vivo. Mice were first implanted with MBT-2 cells and then treated with EGCG or EGCG-nanogold. In the early and late interventions, EGCG and/or nanogold were administrated orally in mice. Refer to FIG. 5 for a schematic diagram of the tumor volume in mice orally treated with EGCG and/or nanogold. The result showed that the combined treatment can significantly reduce the tumor volume in 24 days after the mice implanted with the cancer graft. Additionally, the mean tumor volume was significantly reduced in the prevention and treatment groups that received the combined treatment (75% and 50%, respectively, at day 29).

Figure 6:
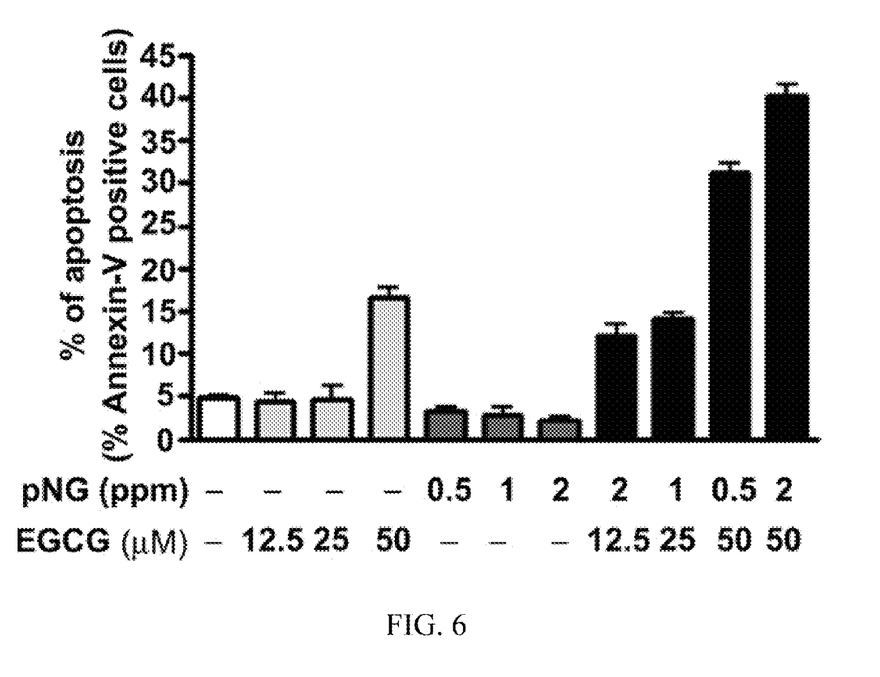
FIG. 6 is a schematic diagram of MBT-2 cells cultured with or without EGCG and/or nanogold for 24 hours, followed by Annexin-V staining for the detection of apoptosis.

4. The Effect of EGCG Plus Nanogold Treatment on Induction of Apoptosis in Bladder Cancer Cells Cell apoptosis features some morphological alterations, such as chromatin condensation, membrane blebbing, internucleosomal degradation of DNA, and apoptotic body formation. Previous study reported that EGCG can induce apoptosis via the PI3K/Akt pathway and Bcl-2 family proteins in T24 human bladder cancer cells. To determine whether the tumor cell cytotoxicity of EGCG and/or nanogold in MBT-2 cells is also mediated by the same mechanism, MBT-2 cells were first treated with EGCG (12.5, 25 and 50 M) or nanogold (0.5, 1 and 2 ppm) for 24 hours. The cells in test were subjected to flow cytometry analysis, whereby apoptotic bodies can be detected by Annexin-V and PI staining Refer to FIG. 6 for a schematic diagram of MBT-2 cells cultured with or without EGCG and/or nanogold for 24 hours, followed by Annexin-V staining for the detection of apoptosis. As a result, the apoptotic cells obtained from EGCG and/or nanogold treatments were quantified (%), for which MBT-2 cells were assayed using Annexin-V. In 48 hours, the percentage of Annexin-V-positive cells was found to increase 2.5-fold, from 16.6% of cells with addition of EGCG to 40.2% of cells with addition of EGCG plus nanogold.

Figure 7:
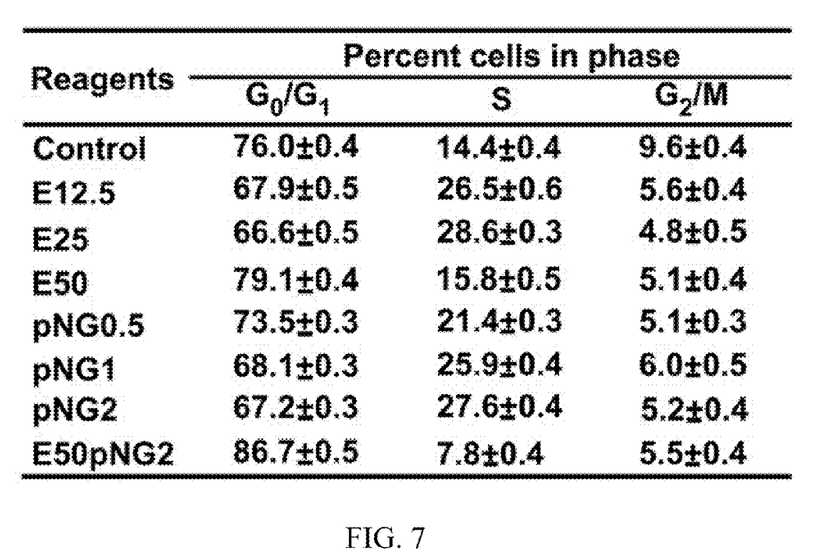
FIG. 7 is a table of the cell cycle of MBT-2 cell treated by various concentrations of EGCG and nanogold.

Following, the mechanism of the EGCG and nanogold mediated cell apoptosis was investigated. Refer to FIG. 7 for a table of the cell cycle of MBT-2 cell treated by various concentrations of EGCG and nanogold. As a result, the MBT-2 cells treated with EGCG or nanogold seem to be arrested in the S phase of cell cycle. The MBT-2 cells otherwise underwent G0/G1 arrest when the doses of EGCG (50 µM) and nanogold (2 ppm) were increased.

Figure 8:
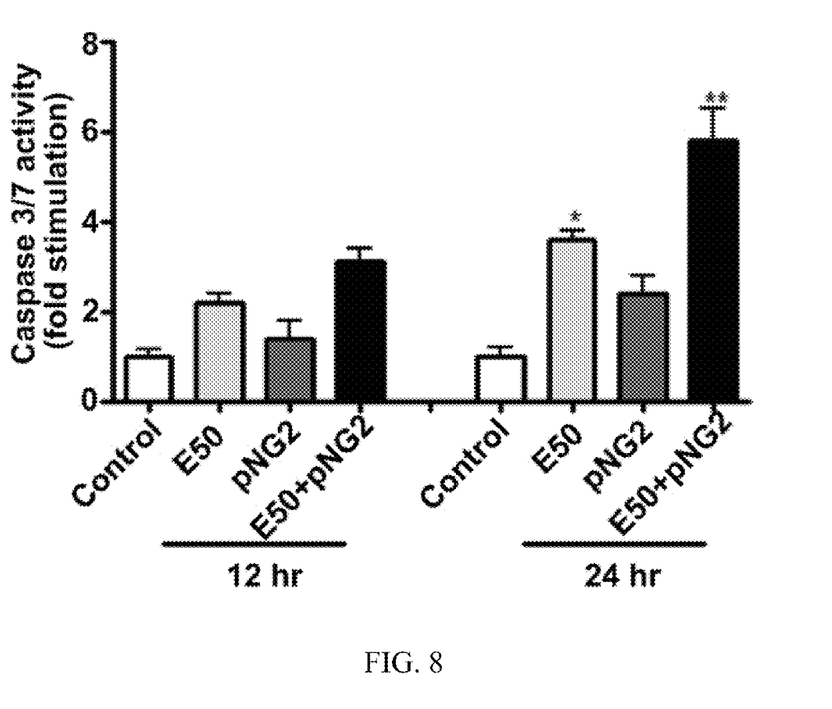
FIG. 8 is a schematic diagram of Caspase-3/7 activity after EGCG and/or nanogold treatment for 12 and 24 hours.

To assure that the EGCG and nanogold mediated apoptosis are triggered by the caspase effectors, we then examined expressions of the apoptosis-dependent enzymes caspase-3 and -7. Refer to FIG. 8 for a schematic diagram of Caspase-3/7 activity after EGCG and/or nanogold treatment for 12 and 24 hours. The expressions of caspase-3 and -7 were found to significantly increase, when MBT-2 cells were treated with EGCG. And, the expressions of caspase-3 and -7 in the cells treated with the combination of EGCG and nanogold (5.81±0.70-fold increase versus the vehicle-alone controls, $p<0.01$) were found to be relatively higher than that treated with EGCG alone (2.42±0.43-fold increase, $p<0.05$).

5. Stability of EGCG-Nanogold Over Wide Range of pH Conditions

Figure 9:
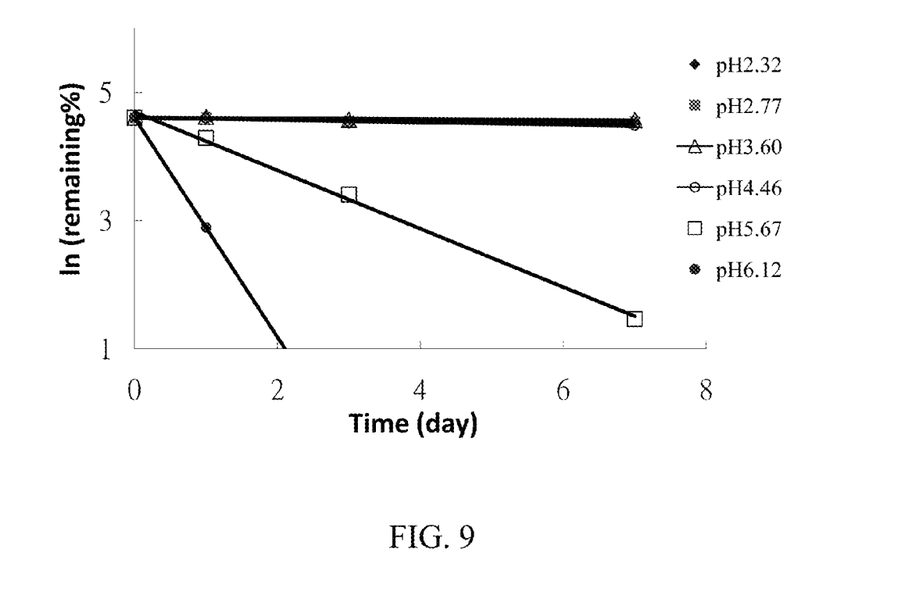
FIG. 9 is a schematic diagram of the influence of pH on physical nano-complexes dissociation over time.

For various therapeutic and biomedical applications, we performed stability analysis of EGCG-nanogold by monitoring EGCG by HPLC over a reasonable period of time and under pH conditions ranging from 2.32 to 6.12. Refer to FIG. 9 for a schematic diagram of the influence of pH on EGCG-nanogold dissociation over time. The figure shows the dissociation patterns of EGCG from EGCG-nanogold complexes after incubation at varied pH at 40° C. for 7 days. The results indicated that EGCG-nanogold was easily dissociated into EGCG at pH 6.12 and 5.67.

Figure 10:
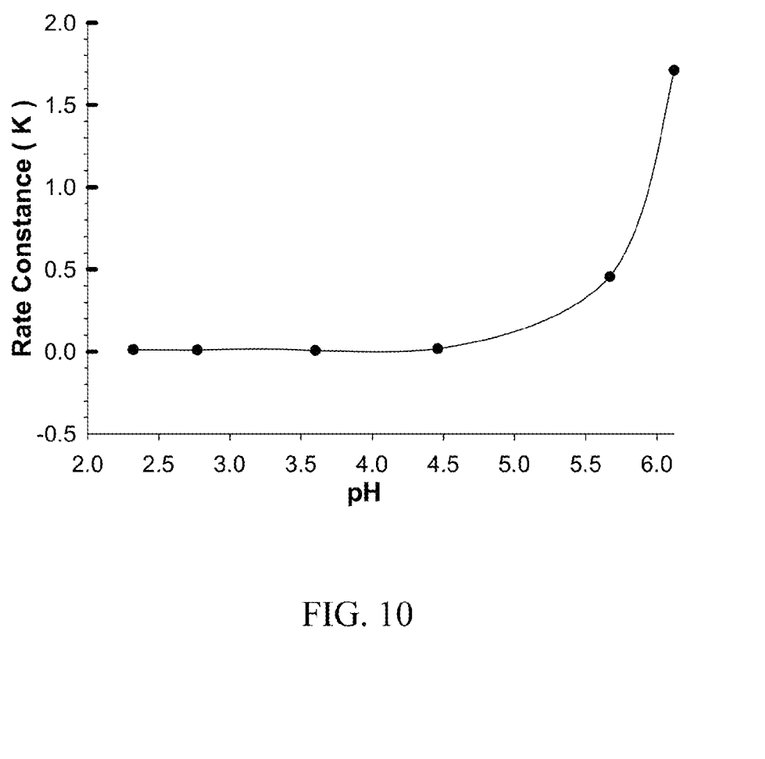
FIG. 10 is a schematic diagram of the dissociation rate constant (k) of EGCG-nanogold complexes under various pH value conditions.

Refer to FIG. 10 for a schematic diagram of the dissociation rate constant (k) of EGCG-nanogold under various pH value conditions. The k for pH 2.32, 2.77, 3.60, 4.46, 5.67, and 6.12 were 0.0118, 0.0097, 0.0062, 0.018, 0.4553, and 1.7109 (1/day). Such significant changes at a pH>4 indicated a greater instability of EGCG-nanogold compared with borohydrate or citrate-reduced nanogold aggregates. However, it should be noted that EGCG-nanogold are highly stable over a reasonable period of time at a pH<4. These results indicated the high potential utility of these nanoparticles for drug delivery applications. In here, EGCG-nanogold complex was highly stable under acidic conditions. EGCG/nanogold hybrid self-assembly was likely due to hydrogen bonding and their electrostatic affinity.

By the detailed description of the overall structure and technical content of the present invention, the following advantages of the present invention can be derived:

EGCG-nanogold provided by the present invention can prevent and treat various cancers, such as bladder cancer, skin cancer, stomach cancer, colon cancer, breast cancer, prostate cancer, oral cancer, and lung cancer, and the effect of EGCG-nanogold is better than that of EGCG or nanogold alone.

The present invention can adjust and optimize the ratio of EGCG to nanogold, so as to prevent and treat various cancers effectively.

The manufacturing method provided by the present invention can enhance the binding level, so as to stabilize the treating effect and elongate the acting time to cancer cells.

It should be understood that the embodiments of the present invention described herein are merely illustrative of the technical concepts and features of the present invention and are not meant to limit the scope of the invention. Those skilled in the art, after reading the present disclosure, will know how to practice the invention. Various variations or modifications can be made without departing from the spirit of the invention. All such equivalent variations and modifications are intended to be included within the scope of the invention.

As a result of continued thinking about the invention and modifications, the inventors finally work out the designs of the present invention that has many advantages as described above. The present invention meets the requirements for an invention patent, and the application for a patent is duly filed accordingly. It is expected that the invention could be examined at an early date and granted so as to protect the rights of the inventors.

What is claimed is:

1. A composition, comprising:
an epigallocatechin-3-gallate (EGCG); and
a nanogold having a particle size ranged from 1.0 nm (nano meter) to 50.0 nm;
wherein the composition has a part per million (ppm) ratio of the EGCG to the nanogold ranging from 23:0.5 to 23:10.

2. The composition according to claim 1, wherein:
the ppm ratio of the EGCG to the nanogold is 23:2.5.

3. The composition according to claim 1, wherein:
the ppm ratio of the EGCG to the nanogold is 5.72:2.

4. A process for manufacturing a composition, comprising:
(1) providing a EGCG and a nanogold; and
(2) mixing the EGCG and the nanogold, wherein:
the ppm ratio of the EGCG to the nanogold is between 23:0.5 to 23:10, and the nanogold having a particle size ranging from 1.0 nm to 50.0 nm.

5. The process according to claim 4, further comprising:
(3) centrifuging the product of step (2) at 14,000 rpm for 2 hours;
(4) removing the supernatant from step (3); and
(5) resuspending a pellet obtained from step (3).

6. The process according to claim 4, wherein:
the ppm ratio of the ECGC to the nanogold is 23:2.5.

7. The process according to claim 4, wherein:
the mixing of the EGCG and the nanogold is achieved by a physical process.

8. The process according to claim 7, wherein:
the physical process is an ultrasonication.

9. The process according to claim 8, wherein:
the ultrasonication is to vibrate the mixture by ultrasonic at room temperature for 5 minutes.

* * * * *